United States Patent [19]

Miyake

[11] 4,259,165
[45] Mar. 31, 1981

[54] DISSOLVED OXYGEN PROBE

[75] Inventor: Yoshihiro Miyake, Yokohama, Japan

[73] Assignee: Hokushin Electric Works, Ltd., Tokyo, Japan

[21] Appl. No.: 102,148

[22] Filed: Dec. 10, 1979

[30] Foreign Application Priority Data

Dec. 20, 1978 [JP] Japan .......................... 53-177918[U]

[51] Int. Cl.³ ............................................. G01N 27/46
[52] U.S. Cl. ................................. 204/195 P; 204/1 T
[58] Field of Search .............................. 204/1 P, 195 P

[56] References Cited

U.S. PATENT DOCUMENTS

| | | |
|---|---|---|
| 3,239,444 | 3/1966 | Heldenbrand . |
| 3,260,656 | 7/1966 | Ross ..................... 204/1 P |
| 3,272,725 | 9/1966 | Garst .................. 204/195 P |
| 3,328,277 | 6/1967 | Solomons et al. ............... 204/195 P |
| 3,454,485 | 7/1969 | Hauk et al. ........................ 204/195 P |
| 3,510,421 | 5/1970 | Gealt . |
| 3,616,410 | 10/1971 | Shtoffer et al. .................. 204/195 P |
| 3,748,245 | 7/1973 | Feren et al. ...................... 204/195 P |
| 3,948,746 | 4/1976 | Poole . |
| 4,078,981 | 3/1978 | Neti et al. ......................... 204/195 P |

Primary Examiner—T. Tung
Attorney, Agent, or Firm—Michael Ebert

[57] ABSTRACT

A probe submersible in a liquid to continuously analyze the concentration of a gas such as oxygen dissolved therein. The probe is constituted by a casing having an open mouth covered by a gas-permeable membrane to define a chamber filled with an electrolyte. Disposed within the chamber is a measuring electrode and a counter-electrode, the front face of the measuring electrode being slightly spaced from the rear surface of the membrane to create a gap that is filled by the electrolyte. Holes are formed in the measuring electrode to permit the passage of electrolyte between the front and rear faces thereof, the rear face being coated with an insulating layer to prevent an electrochemical reaction between this face and the electrolyte whereby the probe is then insensitive to dissolved gas contained in the electrolyte and responds only to gas contained in the liquid being analyzed. The walls of the holes may also be lined with an insulation layer for the same purpose.

5 Claims, 4 Drawing Figures

U.S. Patent    Mar. 31, 1981    4,259,165
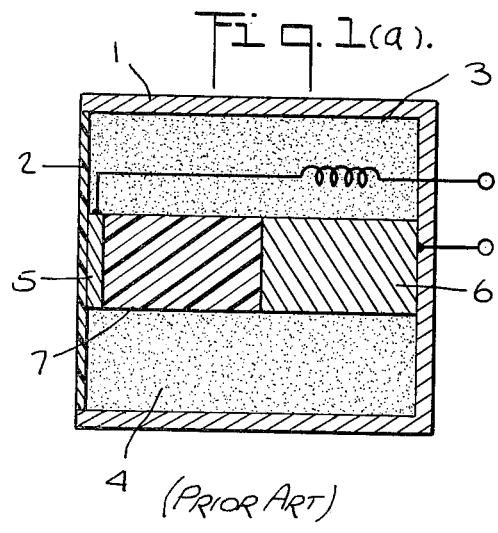
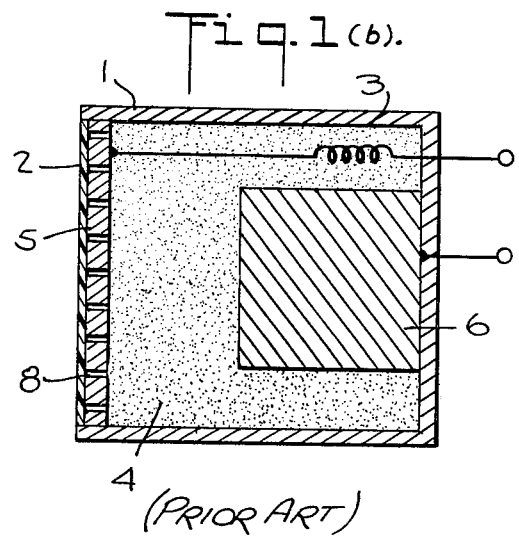
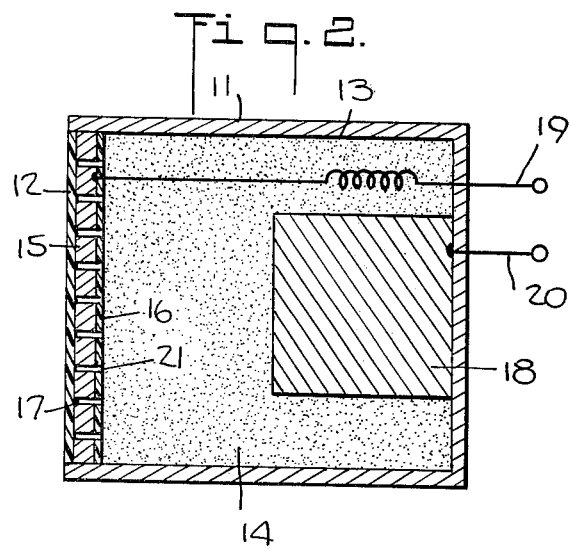
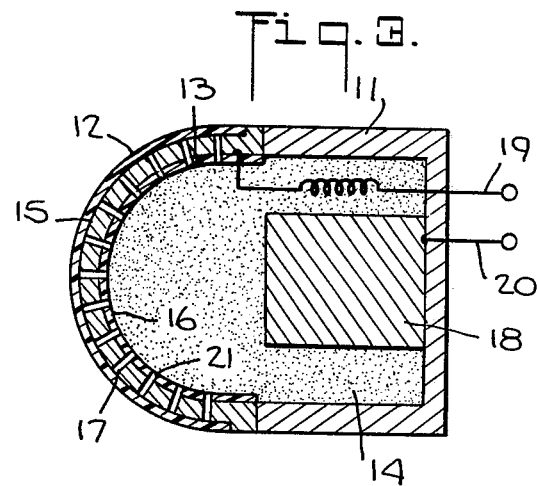

DISSOLVED OXYGEN PROBE

BACKGROUND OF INVENTION

This invention relates generally to a submersible probe adapted to continuously analyze the concentration of a gas such as oxygen dissolved in a liquid, and more particularly to a probe of this type having an improved measuring electrode structure.

In liquid wastes, the factor which determines whether biological changes are being brought about by aerobic or by anaerobic organisms is dissolved oxygen. Aerobic activity requires free oxygen and produces innocuous end products, whereas anaerobic activity can utilize chemically bonded oxygen such as sulfates to produce end products which are obnoxious. Because both types are ubiquitous in nature, it is vital in waste treatment that conditions conducive to aerobic activity be encouraged, for otherwise anaerobic organisms will take over.

Thus in aerobic treatment processes intended to purify sewage and industrial wastes, the present practice is to continuously measure the dissolved oxygen in order to monitor and maintain proper aerobic conditions. Since all aerobic treatment techniques depend upon the presence of dissolved oxygen, the continuous testing thereof is essential when regulating the rate of aeration not only to insure that the supply of oxygen is adequate to maintain aerobic conditions, but also to prevent excessive use of energy needed for aeration.

The need for dissolved oxygen measurement is by no means limited to sanitary engineering, for oxygen is a significant factor in iron and steel corrosion, such as in steam boilers. Thus in control systems for removing oxygen from boiler-feed waters, it is customary in the power industry to measure the dissolved oxygen concentration.

Dissolved oxygen probes of the electrochemical type are well known. Some of these probes exploit the magnitude of the depolarizing effect of oxygen on a special galvanic cell. Thus in U.S. Pat. Nos. 3,510,421 and 3,239,444 there are disclosed embodiments of electrochemical cells which are immersible in liquid for measuring the concentration of dissolved oxygen. In its simplest form, the cell is constituted by an anode or counter-electrode and a cathode or measuring electrode bridged by an electrolyte. The cell is adapted by means of a diffusion membrane covering the measuring electrode and permeable only to gases but impermeable to liquids to receive a sample of oxygen. Upon the entry of the sample, a chemical reaction occurs, modifying the electrical characteristics of the cell. Also of background interest is the 1976 patent to Poole, U.S. Pat. No. 3,948,746 and the prior art cited therein.

SUMMARY OF INVENTION

The main object of this invention is to provide an improved probe of high sensitivity which is submersible in a liquid to continuously analyze the concentration of a gas such as oxygen dissolved therein.

More particularly, an object of this invention is to provide a probe of the above type having an improved measuring electrode to render the probe insensitive to dissolved oxygen contained in the electrolyte, whereby the probe affords a true indication of the concentration of dissolved oxygen in the liquid being analyzed.

Briefly stated, these objects are attained in a probe submersible in a liquid to continuously analyze the concentration of a gas such as oxygen dissolved therein. The probe is constituted by a casing having an open mouth covered by a gas-permeable membrane to define a chamber filled with an electrolyte. Disposed within the chamber is a measuring electrode and a counter-electrode, the front face of the measuring electrode being slightly spaced from the rear surface of the membrane to create a gap that is filled by the electrolyte.

Holes are formed in the measuring electrode to permit the passage of electrolyte between the front and rear faces thereof, the rear face being coated with an insulating layer to prevent an electrochemical reaction between this face and the electrolyte whereby the probe is then insensitive to dissolved gas contained in the electrolyte and responds only to gas contained in the liquid being analyzed. The walls of the holes may also be lined with an insulation layer for the same purpose.

OUTLINE OF DRAWINGS

For a better understanding of the invention as well as other objects and further features thereof, reference is made to the following detailed description to be read in conjunction with the accompanying drawings wherein:

FIG. 1(a) schematically illustrates, in a longitudinal cross section, one known form of submersible probe for analyzing the concentration of dissolved oxygen;

FIG. 1(b) schematically illustrates, in a longitudinal cross section, another known form of such probe;

FIG. 2 is a longitudinal cross section of one preferred embodiment of a probe in accordance with the invention; and FIG. 3 is a longitudinal cross section of another preferred embodiment.

DESCRIPTION OF INVENTION

Prior Art

Referring now to FIG. 1(a), the prior art probe shown therein includes a cylindrical casing 1 having an open mouth, one end of which is covered by a membrane 2 to define an internal chamber 3. Chamber 3 is filled with an electrolyte 4.

Disposed within chamber 3 is a measuring electrode 5 acting as a cathode and a counter-electrode 6, counter-electrode 6 being attached to the rear wall of the casing electrode. Measuring electrode 5 is placed with its front face adjacent the rear surface of membrane 2 with a very small gap therebetween whereby a thin layer of electrolyte 4 is formed in the gap. As a consequence, a current is caused to flow in the electrolytic path between measuring electrode 5 and counter-electrode 6 with an intensity proportional to the dissolved oxygen concentration in the fluid impinging on the outer surface of membrane 2.

In the probe arrangement illustrated in FIG. 1(a), in order that electrolyte 4 may enter the small gap between measuring electrode 5 and membrane 2 to form a thin electrolyte layer therein, the surface area of the measuring electrode must be limited. Hence with a measuring electrode 5 of limited surface area, it is necessary to attach electrode 5 to the end wall of casing 1 through a supporting insulator interposed between electrode 5 and counter-electrode 6.

Because of the reduced surface area of the measuring electrode 5 in the probe illustrated in FIG. 1(a), a decreased output is obtained; hence a probe of high-sensitivity characteristic is not realizable.

In the prior art probe arrangement disclosed in FIG. 1(b), the surface of the measuring electrode diameter is equal to the internal diameter of casing 1; hence the surface area of this electrode is much greater than in the probe shown in FIG. 1(a), thereby enhancing the sensitivity of the probe. However, in the FIG. 1(b) arrangement, in order to provide an enlarged surface area, it is necessary to have an array of small holes formed in electrode 5. One side of electrode 5 faces membrane 2, while the other side which faces counter-electrode 6 also lies in conductive contact with electrolyte 4 and thereby behaves as an electrode.

As a consequence, the probe not only responds to the concentration of dissolved oxygen in the fluid in which the probe is immersed but also to the concentration of dissolved oxygen contained in electrolyte 4. Thus even if dissolved oxygen is not present in the fluid in contact with the surface of membrane 2, measuring electrode 5 nevertheless reacts as if oxygen were dissolved therein. Moreover, as the electrochemical reaction proceeds, the amount of dissolved oxygen in electrolyte 4 diminishes, thereby giving rise to zero point variations.

First Embodiment

To overcome this drawback which is characteristic of probes of the prior art type shown in FIGS. 1(a) and 1(b), in a probe in accordance with the invention, small holes are formed in a measuring electrode of a large surface area to permit the passage therethrough of the electrolyte, the reverse face of the measuring electrode and the walls of the holes being coated with a layer of insulation to isolate the electrolyte therefrom and render the probe insensitive to gas contained in the electrolyte.

In the first embodiment of this probe shown in FIG. 2, there is provided a cylindrical casing 11 having an open mouth covered by a membrane 12 to define an internal chamber 13 which is filled with an electrolyte 14. Cathode 15 serving as a measuring electrode and having a diameter equal to the internal diameter of the casing is disposed with its front face in a position slightly spaced from the rear surface of membrane 12, the periphery of this electrode being secured to the casing. Measuring electrode 15 has bored therethrough an array of small holes 17.

The rear face of electrode 15, which is on the side opposite membrane 12, is covered with a thin film 16 of insulating material, such as a film of synthetic resin material, the film having small holes 21 therein in registration with holes 17 in the electrode. Rather than cover the rear face of electrode 12 with a thin film, it may be coated with an insulating layer of synthetic resin having small holes 21 bored therein.

Electrolyte 14 passes through small holes 17 in the electrode and small holes 21 aligned therewith in the insulating layer to enter into the gap between the rear surface of membrane 12 and the front face of measuring electrode 15, thereby forming a thin electrolytic layer in this cap. Anode 18 secured to the rear wall of casing 11 serves as the counter-electrode. Leads 19 and 20 are connected respectively to measuring electrode 15 and counter-electrode 18.

In operation, when the probe is immersed in fluid, the fluid is in contact with the outer surface of membrane 12. When the fluid contains a dissolved oxygen component, this component reacts with the front face of measuring electrode 15 through the gas-permeable membrane 12. As a consequence, a current is caused to flow between measuring electrode 15 and counter-electrode 18 whose intensity is a function of the concentration of this component.

Since the rear face of measuring electrode 15 is covered with an insulating layer 16, even if the same component present in the fluid being analyzed is also dissolved in electrolyte 14 within the casing, no reaction takes place between the electrolyte component and the measuring electrode. Hence the resultant fluid analysis is substantially unaffected by a dissolved component in the electrolyte, and the probe is not subject to zero point variations which give rise to spurious readings.

Second Embodiment

In the probe shown in FIG. 3, membrane 12 and measuring electrode 15 are constructed in hemispherical or dome-like form, so that their surface areas are large relative to the diameter of casing 11 to which these members are attached. Because of the enlarged area, the probe is of heightened sensitivity even in the case of a small probe size. The other parts of this probe are identical to those designated by the same reference numerals in FIG. 2 and need not, therefore, be described in further detail.

Modifications

In the first and second embodiments, the rear face of electrode 15 is covered with an insulating layer 16. Where the number of small holes 17 bored in electrode 15 is large, it is desirable in this instance to line the walls of these holes with insulating material so that no reaction occurs between the electrolyte and the exposed metal of the hole walls.

Thus by insulating the rear face of the electrode and the hole walls, one obtains a probe of the membrane type which is capable of accurately metering the concentration of dissolved oxygen in the liquid in which the probe is immersed, the probe being highly sensitive and yet being free from zero point variations; for the probe is effectively isolated from dissolved oxygen contained in the electrolyte.

While there have been shown and described preferred embodiments of a dissolved oxygen probe in accordance with the invention, it will be appreciated that many changes and modifications may be made therein without, however, departing from the essential spirit thereof.

I claim:

1. A galvanic cell probe submersible in a liquid to continuously analyze the concentration of a gas, such as oxygen, dissolved therein, said probe comprising:

A a casing having an open mouth covered by a gas permeable membrane to define a chamber filled with an electrolyte;

B a measuring electrode disposed in said chamber with its front face closely adjacent the inner surface of the membrane to create a gap that is occupied by the electrolyte, said measuring electrode having holes therein to form an electrolyte passage between the front face and the rear face of the electrode, said rear face having an insulating layer thereon to prevent a reaction between the rear face and the electrolyte whereby the probe is rendered substantially insensitive to dissolved gas contained in the electrolyte and responds only to dissolved gas contained in the liquid being analyzed, said insulating layer having holes therein all of which being in registration with all of the holes in the measuring electrode on a one-to-one basis; and C a counter-electrode disposed in said chamber whereby the current passing between the measuring electrode and the counter-electrode through said electrolyte as a result of galvanic action is a function of the concentration of dissolved gas in said liquid.

2. A probe as set forth in claim 1, wherein said holes are lined with an insulation layer.

3. A probe as set forth in claim 1, wherein said casing has a rear wall and said counter-electrode is mounted thereon.

4. A probe as set forth in claim 1, wherein said casing is cylindrical in form and said measuring electrode is a metal disc secured at its periphery to the inner wall of the casing adjacent the mouth thereof.

5. A probe as set forth in claim 1, wherein said casing is cylindrical in form and said measuring electrode is in the form of a dome whose rim is secured to said casing at the mouth thereof, said membrane having a form corresponding to that of said measuring electrode.

* * * * *